United States Patent [19]

Kerimis et al.

[11] Patent Number: 4,837,321

[45] Date of Patent: Jun. 6, 1989

[54] PROCESS FOR THE PREPARATION OF POLYISOCYANATES CONTAINING ISOCYANURATE GROUPS

[75] Inventors: Dimitrios Kerimis, Cologne; Hanns P. Müller, Odenthal, both of Fed. Rep. of Germany

[73] Assignee: Bayer Aktiengesellschaft, Bayerwerk, Fed. Rep. of Germany

[21] Appl. No.: 937,952

[22] Filed: Dec. 4, 1986

[30] Foreign Application Priority Data

Dec. 12, 1985 [DE] Fed. Rep. of Germany ....... 3543925

[51] Int. Cl.⁴ .......................................... C07D 251/34
[52] U.S. Cl. .................... 544/193; 544/221; 544/222; 528/45; 528/51; 521/107; 521/108
[58] Field of Search ............. 544/221, 222, 193; 528/45; 521/107

[56] References Cited

U.S. PATENT DOCUMENTS

| | | | |
|---|---|---|---|
| 3,394,111 | 7/1968 | Liebsch | 260/77.5 |
| 3,919,218 | 11/1975 | Schmitt et al. | 260/248 |
| 4,066,629 | 1/1978 | Edelman | 260/77.5 |
| 4,115,373 | 9/1978 | Henes et al. | 528/48 |
| 4,252,923 | 2/1981 | Konig et al. | 525/452 |
| 4,255,569 | 3/1981 | Müller | 544/193 |
| 4,324,879 | 4/1982 | Bock et al. | 528/45 |
| 4,499,253 | 2/1985 | Kerimis et al. | 528/45 |

FOREIGN PATENT DOCUMENTS 1244416  9/1971  United Kingdom .

OTHER PUBLICATIONS

J. H. Saunders & K. C. Frisch, "Polyurethanes Chemistry and Technology", pp. 94 et seq. (1962).
A. Farkas and G. A. Mills, "Advances in Catalysis", vol. 13, pp. 393 et seq. (1962).
J. Kresta, R. Chang, S. Kathiriya and K. Frisch, "Makromol Chemie", 180, p. 1081 (1979).
Chemical Abstracts, vol. 93, Sep. 1980, D. M. Yukhnovich et al., "Triarylisocyanurate", Abstract No. 132518e.

*Primary Examiner*—John M. Ford
*Attorney, Agent, or Firm*—Gene Harsh; Joseph C. Gil; Thomas W. Roy

[57] ABSTRACT

The present invention is directed to a process for the preparation of isocyanurate group-containing polyisocyanates by trimerizing a portion of the isocyanate groups of an organic polyisocyanate and terminating the trimerization reaction by the addition of a catalyst poison, characterized in that the trimerization catalyst used is a quaternary phosphonium salt of a tertiary phosphine and an alkylating ester of an acid of phosphorus. The present invention also relates to the use of the polyisocyanates obtained according to this process, optionally, in a form that has been freed from excess starting polyisoyanate and/or optionally blocked with blocking agents for isocyanate groups as the isocyanate component for the preparation of polyisocyanate polyaddition products, preferably polyurethanes.

9 Claims, No Drawings

PROCESS FOR THE PREPARATION OF POLYISOCYANATES CONTAINING ISOCYANURATE GROUPS

BACKGROUND OF THE INVENTION

1. Field of the Invention

The present invention relates to a new process for the preparation of polyisocyanates containing isocyanurate groups by the catalytic trimerization of monomeric polyisocyanates using novel trimerization catalysts and to their use as the isocyanate component for the preparation of polyisocyanate polyaddition products, preferably polyurethanes.

2. Description of the Prior Art

Numerous catalysts for the trimerization of organic isocyanates, in particular polyisocyanates, are known (J. H. Saunders and K. C. Frisch, Polyurethanes Chemistry and Technology, page 94 et seq (1962)). Strong organic bases are suitable as trimerization catalysts, e.g. carboxylic acid metal salts which are alkaline in nature, metal alcoholates, metal phenolates, alkali metal carbonates and tertiary amines.

The catalysts are frequently used in combination with one another or together with cocatalysts such as mono-N-substituted carbamic acid esters (A. Farkas and G. A. Mills, Advances in Catalysis, Vol. 13, 393 (1962)).

In the more recent state of the art processes, the trimerization catalysts used are special organic bases some of which are required to be prepared by elaborate methods of synthesis.

Thus, for example, the trimerization of aromatic polyisocyanates is catalyzed with Mannich bases (DE-OS No. 2,551,634 and DE-OS No. 2,641,380) or tertiary phosphines. When phosphines are used, uretdiones are first formed and then converted to the isocyanurate in a second reaction phase (DE-OS No. 1,201,992). The trimerization of (cyclo)aliphatic diisocyanates has in recent times frequently been catalyzed with organic bases having a betaine structure such as quaternary ammonium hydroxides (EP-A No. 010,589 and EP-A No. 009,694): aminimides (J. E. Kresta, R. J. Chang, S. Kathiriya and K. C. Frisch, Makromol. Chem. 180, 1081 (1979)): and aziridine derivatives in combination with tertiary amines (DE-OS No. 2,325,826).

The use of the quaternary ammonium salts obtained from tertiary amines and alkylating esters of acids of phosphorus as trimerization catalysts is described in DE-OS No. 3,227,489.

The present invention provides a new class of valuable trimerization catalysts which are distinguished by the combination of numerous remarkable advantages:

1. The new catalysts are suitable for trimerizing both aromatic and aliphatic polyisocyanates.
2. Both the new catalysts and the products of their reaction with the catalyst poisons described below are soluble in the starting materials and end products of the process according to the invention so that elaborate procedures for separation are obviated.
3. Trimerization with the aid of the new catalysts may be carried out either solvent-free or in the presence of solvents at comparatively low temperatures so that pale yellow, clear, low viscosity polyisocyanates containing isocyanurate groups are obtained as products of the process.
4. The slightly exothermic trimerization reaction can be safely and easily controlled both when carried out continuously and when carried out batchwise.
5. The catalysts can be easily and inexpensively prepared and are almost odorless.

SUMMARY OF THE INVENTION

The present invention is directed to a process for the preparation of polyisocyanates containing isocyanurate groups by trimerizing a portion of the isocyanate groups of organic polyisocyanates and terminating the trimerization reaction by the addition of a catalyst poison, characterized in that the trimerization catalysts used are quaternary phosphonium salts of tertiary phosphines and alkylating esters of acids of phosphorus.

The present invention also relates to the use of polyisocyanates containing isocyanurate groups obtainable by this process, optionally in a form freed from excess starting polyisocyanates and/or optionally blocking with blocking agents for isocyanate groups, as the isocyanate component for the preparation of polyisocyanate polyaddition products, preferably polyurethanes.

DETAILED DESCRIPTION OF THE INVENTION

The new trimerization catalysts which are essential to the invention are quaternary phosphonium salts, i.e. phosphonium salts containing no NH bonds, constituting reaction products of (i) tertiary phosphines with (ii) alkylating esters of acids of phosphorus.

Any tertiary phosphine may be used as catalyst component (i). The tertiary phosphines preferably have a molecular weight of 76 to about 790, in particular 202 to about 280.

The following are examples of phosphines of this kind: trimethylphosphine, triethylphosphine, tricyclohexylphosphine, trioctylphosphine, tristearylphosphine and, preferably, tri-n-butylphosphine, and triphenylphosphine. Among these, tri-n-butylphosphine is particularly suitable.

Catalyst component (ii) is based on neutral, alkylating esters of inorganic or organic acids of phosphorus, especially the alkyl esters of phosphoric acid conforming to this definition and optionally containing inert substituents, in particular the alkyl esters of aromatic or aliphatic phosphonic acids. Alkyl esters of other acids of phosphorus conforming to the above definition, e.g. the alkyl esters of phosphorous acid, phosphinic acids, phosphonous and phosphinous acids are suitable in principle, but less preferred. It is preferable to use alkyl esters having 1 to 4 carbon atoms in the individual alkyl groups.

Phosphonic acid esters corresponding to the formula

are particularly preferred. In the above formula,

R denotes an aromatic hydrocarbon group having 6 to 10 carbon atoms and optionally having inert substituents, in particular a phenyl group, or an aliphatic hydrocarbon group, in particular an alkyl group having 1 to 4 carbon atoms, and R' denotes identical or different aliphatic hydrocarbon groups, in particular alkyl groups having 1 to 4 carbon atoms.

The following examples of suitable catalyst components (ii): triethylphosphate, dimethyl-benzylphosphate, trimethylphosphate, benzene phosphonic acid dimethylester, p-toluene phosphonic acid diethylester, methane phosphonic acid dimethylester, n-butanephosphonic acid diethylester, ethanephosphonic acid diethylester and ethanephosphonic acid dimethylester.

For the preparation of the catalysts according to the invention, the individual components (i) and (ii) are reacted together in the quantities required to provide at least one mol of component (ii) to each gram equivalent of tertiary phosphorus of component (i). Component (ii) may be used in any desired excess amount and is preferably removed after the alkylating reaction, for example by distillation. The individual components (i) and (ii) are preferably reacted together solvent-free at a temperature of about 50° to 200° C., preferably about 80° to 180° C., for about 0.5 to 10 hours.

It is frequently advantageous to carry out the reaction in an inert gas atmosphere and/or under pressure. The reaction time and temperature depend, of course, primarily upon the reactivity of the individual components (i) and (ii).

The trimerization catalysts according to the invention obtained as described above may, of course, be used for the preparation of any isocyanurates. This means that the catalysts are suitable not only for the process according to the invention but also, for example, for the preparation of isocyanurates by the trimerization of monoisocyanates.

The catalysts which are essential to this invention are put into the trimerization reaction either solvent-free or as solutions at concentrations of about 0.005 to 95% by weight, preferably about 0.01 to 70% by weight.

Examples of suitable solvents include methanol, ethanol, propanol, ethylene glycol, propanediol-(1,2), propanediol-(1,3), butylene glycol, glycerol, oligoethylene glycols and oligopropylene glycols (degree of oligomerization 2 to 6). The alcohols should be good solvents for the ammonium compounds, but at the same time be to some extent miscible with the isocyanate and have a low viscosity).

Aprotic solvents which are unreactive with isocyanates may also be used. Their $E_T$-value (Ch. Reichardt, Losungsmittel-Effekte in der organischen Chemie, Chem. Taschenbucher, Vol. 4, publishers Verlag Chemie (Weinheim 1969)) should preferably be in the range of 33.5 to 47. Examples include nitriles such as acetonitrile, propionitrile or benzonitrile; nitro compounds such as nitromethane or nitrobenzene; carbonic acid esters such as ethylene or propylene carbonate; ketones such as acetone, acetophenone, butyl methyl ketone or isobutyl methyl ketone, apolar solvents as chlorinated hydrocarbons, e.g. methylene chloride, chloroform, 1,1,1-trichloroethane or trichloroethylene; aromatic hydrocarbons such as benzene, toluene or xylene; and esters such as ethyl acetate, butyl acetate or ethylene glycol monomethyl ether acetate.

Highly polar solvents such as dimethylformamide, N-methylpyrrolidone, tetramethylurea or dimethylsulphoxide could be used in principle, but their use is not recommended for two reasons. Initially, they are difficult to free from by-products such as amines and, secondly, they catalyze side reactions with isocyanate groups which are generally undesirable so that the products obtained from the process according to the invention would not be stable in storage in the presence of such solvents.

When solvents containing hydroxyl groups are used, urethane groups are formed in the process according to the invention by a reaction with a portion of the isocyanate groups in the starting polyisocyanate. This is frequently desirable since such urethane groups have a cocatalytic action. However, the quantity of such solvents used, if they are monohydric alcohols, should however be limited so that the reaction mixture contains at most about 2 mol % of hydroxyl groups, based on the isocyanate groups of the starting polyisocyanate. It is in many cases also advantageous to use polyhydric alcohols such as ethylene glycol or glycerol as hydroxyl-containing solvents for the catalysts according to the invention in order not to reduce the isocyanate functionality of the products by urethane formation. The quantity of such polyhydric alcohols used must, of course, be limited to avoid the formation of difficultly soluble polyurethanes in the products. The quantity of catalysts used for the trimerization reaction according to the invention is generally about 0.005 to 5 mol %, preferably about 0.01 to 2 mol %, based on the starting polyisocyanate which is to be trimerized and on the phosphonium salts formed from components (i) and (ii) without taking into account any excess alkylating esters still present.

If aromatic polyisocyanates are to be trimerized without the presence of solvents, the quantity of catalysts according to the invention is preferably within the range of about 0.01 to 0.02 mol %, whereas, if the aromatic starting polyisocyanate is diluted with a suitable aprotic solvent, then the quantity of catalyst is generally about 0.01 to 0.1 mol %.

If the starting polyisocyanates have exclusively aliphatically bound isocyanate groups the quantity of catalyst is generally about 0.05 to 0.3 mol %; whereas, when starting polyisocyanates have cycloaliphatically bound isocyanate groups, then the quantity of catalyst used is preferably about 0.3 to 2.0 mol %, all of these percentages being based, as indicated above, on the quantity of starting polyisocyanate and the quantity of phosphonium salt.

Any organic polyisocyanates may be used as starting materials for the trimerization reaction. The new catalysts according to the invention are suitable in particular for the partial trimerization of the isocyanate groups of diisocyanates having a molecular weight of about 140 to 300 and having aromatically, aliphatically or cycloaliphatically bound isocyanate groups. Examples include tetramethylene diisocyanate, hexamethylene diisocyanate, 1-isocyanato-3,3,5-trimethyl-5-isocyanatomethyl-cyclohexane (isophorone diisocyanate, abbreviated: IPDI), 2,4- and/or 2,6-diisocyanatotoluene, 2,4'- and/or 4,4'-diisocyanatodiphenylmethane, 2,4'-diisocyanatodicyclohexylmethane, 1-methyl-2,4-diisocyanatocyclohexane, lysine ester diisocyanates, p-xylylene diisocyanate and any mixtures of such diisocyanates. Mixtures of the aromatic diisocyanates exemplified above with aliphatic diisocyanates mentioned as examples in proportions by weight of about 1:3 to 3:1 are particularly suitable. Higher functional polyisocyanates such as polyisocyanate mixtures obtained by the phosgenation of aniline/formaldehyde condensates may be used as starting polyisocyanates for the process according to the invention. It is possible in principle although less preferred to use isocyanate prepolymers as starting polyisocyanates for the process according to the invention, i.e. to use reaction products of excess quantities of the diisocyanates mentioned above as examples with difunctional or higher functional compounds containing isocyanate reactive groups. Mixtures of diisocyanates and monoisocyanates may in principle also be used as starting materials for the process according to the invention in order to obtain interesting polyisocyanates with isocyanurate groups in which the isocyanate functionality is reduced by a controlled amount. For this purpose, the di- and monoisocyanates are generally put into the process in a molar ratio of diisocyanate:monoisocyanate of about 1.5:1 to 2.5:1. Suitable monoisocyanates include aliphatic monoisocyanates having 1 to 18, preferably 4 to 8 carbon atoms, such as methyl isocyanate, n-butylisocyanate, n-octylisocyanate and stearylisocyanate as well as aromatic monoisocyanates, in particular phenylisocyanate. 2,4- and/or 2,6-diisocyanatotoluene, hexamethylene diisocyanate and IPDI are preferred starting polyisocyanates for the process according to the invention.

The trimerization reaction may be carried out in the presence or absence of solvents which are inert towards isocyanate groups. Any solvents or solvent mixtures inert to isocyanates and boiling within a range of about 50° C./1013 mbar to 250° C./13.3 mbar are suitable for the process according to the invention. The solvents may be either low to medium boiling or high boiling, depending on the intended field of application of the products obtained according to the invention. Examples of preferred solvents include esters such as ethyl acetate, butyl acetate, ethylene glycol monomethylether acetate and ethylene glycol monoethylether acetate and ketones such as acetone, methyl ethyl ketone, methyl isobutyl ketone, cyclohexanone and methoxyhexanone. Phthalic acid esters such as dibutylphthalate or butylbenzylphthalate, phosphoric acid esters such as tricresylphosphate and alkyl sulphonic acid esters of phenol and of cresol are also suitable. The solubility in diluents such as toluene, xylene or higher aromatic compounds is frequently limited so that the addition of higher proportions of such diluents may lead to cloudiness and precipitation of the reaction products.

The solvents and quantity of solvent used for carrying out the trimerization reaction need not be identical to the solvent and quantity of solvent present in the products according to the invention when they are subsequently used. Thus, the solvent or solvent mixture used for the process may, of course, be partly or completely removed by distillation after completion of the process according to the invention or partly or completely replaced by another solvent. Products which have been prepared solvent-free may, of course, subsequently be dissolved in the solvents mentioned above.

The trimerization reaction is generally carried out within the temperature range of about 0° C. to 200° C., preferably about 10° C. to 100° C. and most preferably about 25° C. to 80° C. When the process according to the invention is carried out in the presence of a solvent, the starting polyisocyanate which is to be trimerized and the solvent are generally put into the process in quantities corresponding to proportions by weight of about 1:4 to 4:1, preferably about 1:2 to 2:1 and most preferably about 0.8:2 to 1.2:0.8.

The quantity of catalyst used depends, as mentioned above, on the nature of the starting polyisocyanate and, of course, on the reaction temperature at which trimerization is carried out. It can be reliably determined by a simple preliminary experiment. Compared with the concentration of catalyst to be used in a solvent-free process, the concentration of catalyst should generally be increased by a factor of about 5 to 15 when solvents are used.

The trimerization reaction may be carried out, for example, according to the following variations.

1. The catalyst or its solution in a suitable solvent is added at room temperature to the polyisocyanate to be trimerized without the addition of any auxiliary solvent for the trimerization reaction. The trimerization reaction generally starts spontaneously. The reaction mixture is subsequently maintained at the desired reaction temperature by external heating until the trimerization reaction is stopped by the addition of a catalyst poison.

2. The polyisocyanate to be trimerized is introduced as a solution in a solvent of the type exemplified above. The trimerization catalyst or a solution thereof is then added to the solution of polyisocyanate. In this variation of the process according to the invention, the temperature of the reaction mixture may also be adjusted if necessary by external heating within the ranges mentioned above. The trimerization reaction is again stopped by the addition of a catalyst poison when the desired degree of trimerization has been reached.

In both of the variations exemplified above, the trimerization reaction is generally stopped at a degree of trimerization of about 10 to 70% (degree of trimerization=percentage of trimerized isocyanate groups based on the total quantity of isocyanate groups present in the starting polyisocyanate). When the process according to the invention is carried out solvent-free with subsequent removal of excess starting polyisocyanate, for example in a thin layer evaporator, the degree of trimerization is generally in the region of about 10 to 40%. When the process according to the invention is carried out in the presence of solvents without subsequent removal of unreacted starting polyisocyanate, the degree of trimerization is generally about 50 to 70%.

Examples of suitable catalyst poisons include acid halides, in particular acid chlorides such as acetyl chloride, benzoyl chloride, terephthaloyl dichloride, phthaloyl dichloride, trichloroacetyl chloride, phosphorus trichloride or phosphorus tribromide. Strong acids which neutralize the catalyst and thus inactivate it may also be used, but are less preferred. Examples of these include sulphuric acid, phosphoric acid, hydrogen chloride, toluene sulphonic acid, methane sulphonic acid, chlorosulphonic acid, nonafluorobutanesulphonic acid and dibutylphosphoric acid. Tosyl isocyanate is also suitable. To inactivate the catalyst, it is sufficient to add 100 to 110 equivalent percent of catalyst poison to the reaction mixture, i.e. in the case of a monofunctional catalyst poison to add 100 to 110 mol %, based on the quaternary phosphonium groups present in the catalyst.

The products of the process according to the invention may be freed in known manner from excess unreacted starting polyisocyanate, for example by thin layer distillation, especially if the trimerization reaction is carried out solvent-free, so that the polyisocyanates with isocyanurate groups may be obtained with a monomeric starting diisocyanate content of less than about 3% by weight, preferably less than about 0.7% by weight.

The products of the process according to the invention may, of course, be masked in known manner with suitable masking agents for isocyanate groups such as phenol, ε-caprolactam, diethylmalonate or ethylacetoacetate.

The products of the process according to the invention and their derivatives obtained by the above mentioned masking reaction are valuable starting materials for the preparation of polyisocyanate polyaddition products, preferably polyurethanes; by reaction with compounds containing at least two isocyanate reactive groups, preferably hydroxyl groups. They are suitable in particular as isocyanate components in two-component polyurethane lacquers.

The possibility of stopping the reaction according to the invention by the addition of acid chlorides was not foreseeable since one would have expected quaternary phosphonium salts of the kind used as catalysts according to the invention to be substantially inert towards acid chlorides.

The invention is further illustrated but is not intended to be limited by the following examples in which all parts and percentages are by weight unless otherwise specified.

EXAMPLES

The following trimerization catalysts according to the invention are used in the examples which follow:

CATALYST I 40.4 parts by weight of tri-n-butylphosphine and 121 parts by weight of methanephosphonic acid diethylester were mixed together and stirred at 100° C. for 16 hours while a light stream of nitrogen was passed through the reaction mixture. The excess methanephosphonic acid dimethylester was then distilled off under vacuum.

54 parts by weight of a medium viscosity colorless and odorless liquid were obtained.

CATALYST II 40.4 parts by weight of tri-n-butylphosphine and 56 parts by weight of trimethylphosphate were mixed together and stirred for 16 hours at 100° C. while a light stream of nitrogen was passed through. The excess trimethylphosphate was then distilled off under vacuum.

65 parts by weight of a medium viscosity colorless and odorless liquid were then obtained.

EXAMPLE 1

500 parts by weight of 2,4-tolylene diisocyanate were dissolved in 500 parts by weight of anhydrous butyl acetate, and 2.5 parts by weight of a 10% by weight solution of catalyst I in ethanol were added at room temperature. The reaction mixture was then stirred at room temperature for 60 hours.

The trimerization reaction was finally stopped by the addition of 4 parts by weight of a 3% by weight solution of benzoyl chloride in anhydrous butyl acetate and the reaction mixture was then stirred for one hour at 60° C.

A clear, pale yellow solution was obtained. The specifications of the solution were as follows:
NCO content: 7.7% by weight
free 2,4-tolylene diisocyanate: 0.35% by weight
viscosity $\eta_{23°\ C.}$: 1700 mPas

EXAMPLE 2

800 ml of hexamethylene diisocyanate (HDI) were introduced into the reaction vessel at room temperature and 12 ml of a 0.5 m solution of catalyst I in ethyl hexanol were added under a light stream of nitrogen. After about 18 to 20 hours, when the isocyanate content is 40 to 41%, the reaction was stopped by the addition of an equivalent quantity of tosyl isocyanate and the almost colorless crude product was distilled in a thin layer evaporator.

A clear, slightly yellowish sump product having the following specifications was obtained:
NCO content: 22.5% by weight
viscosity $\eta_{21°\ C.}$: 1100 mPas

EXAMPLE 3

5 parts by weight of catalyst I were added to 250 parts by weight of isophorone diisocyanate (IPDI) and the reaction mixture was stirred at 100° C. (bath temperature). After 20 hours, during which the reaction temperature was kept constant, the isocyanate content fell to 30%.

EXAMPLE 4

100 parts by weight of phenyl isocyanate were dissolved in 100 parts by weight of toluene.

1 part by weight of catalyst II was added and the reaction mixture is stirred at 60° C. The temperature rose to 70° C. after a short time and the trimer begins to precipitate. Stirring was continued for a further 5 hours at 60° C. to complete the reaction and the crystallizate was then suction filtered and dried under vacuum.

91 parts by weight of triphenyl isocyanurate which melted at 284° C. were obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of an isocyanurate group-containing polyisocyanate which comprises trimerizing a portion of the isocyanate groups of an organic polyisocyanate in the presence of a trimerization catalyst which comprises a quaternary phosphonium salt of a tertiary phosphine and an alkylating ester of an acid of phosphorous and subsequently terminating the trimerization reaction by the addition of the catalyst poison.

2. The process of claim 1 wherein said alkylating ester of an acid of phosphorus is a phosphonic acid ester corresponding to the formula

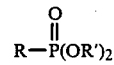

wherein
R represents a phenyl group optionally having an inert substituent or an alkyl group having 1 to 4 carbon atoms, and
R' represents an alkyl group having 1 to 4 carbon atoms.

3. The process of claim 1 wherein said catalyst poison is an organic acid chloride or tosyl isocyanate.

4. The process of claim 2 wherein said catalyst poison is an organic acid chloride or tosyl isocyanate.

5. The process of claim 1 wherein the reaction is carried out at a temperature of about 10° C. to 110° C. and said trimerization catalyst is present in an amount of about 0.01 to 2 mol %, based on said organic polyisocyanate.

6. A process for the preparation of a polyisocyanate polyaddition product which comprises (a) preparing an isocyanurate group-containing polyisocyanate in accordance with the process of claim 1 and (b) reacting said polyisocyanate with a compound containing at least two isocyanate reactive groups.

7. The process of claim 6 wherein said polyisocyanate polyaddition product is a polyurethane.

8. The process of claim 6 wherein said polyisocyanate is blocked with a blocking agent for isocyanate groups.

9. The process of claim 7 wherein said polyisocyanate is blocked with a blocking agent for isocyanate groups.

* * * * *